United States Patent
Johnson et al.

[11] Patent Number: 5,944,023
[45] Date of Patent: Aug. 31, 1999

[54] SYSTEMS AND METHODS FOR DETERMINING THE LOCATION OF AN IMPLANTED DEVICE INCLUDING A MAGNET

[75] Inventors: Theodore A. Johnson, St. Paul; Harry A. Puryear, Shoreview, both of Minn.

[73] Assignee: SIMS Deltec, Inc., St. Paul, Minn.

[21] Appl. No.: 08/946,049

[22] Filed: Oct. 7, 1997

Related U.S. Application Data

[63] Continuation of application No. 08/568,629, Dec. 7, 1995, abandoned.

[51] Int. Cl.$^6$ ........................................... A61B 5/05
[52] U.S. Cl. ........................... 128/899; 600/424; 600/12; 324/207.17
[58] Field of Search ............................ 128/899; 600/407, 600/424, 12; 324/207.17, 207.26, 329, 239; 340/572, 573

[56] References Cited

U.S. PATENT DOCUMENTS

| | | |
|---|---|---|
| 3,133,244 | 5/1964 | Wojtulewicz . |
| 3,189,762 | 6/1965 | Galpin . |
| 3,373,273 | 3/1968 | Schubert . |
| 3,564,402 | 2/1971 | Pittman . |
| 3,622,784 | 11/1971 | Del Guercio . |
| 3,659,588 | 5/1972 | Kahn et al. . |

(List continued on next page.)

FOREIGN PATENT DOCUMENTS

| | | |
|---|---|---|
| 0091577 | 3/1983 | European Pat. Off. . |
| 0320623 | 11/1988 | European Pat. Off. . |
| 0 302 001 A1 | 2/1989 | European Pat. Off. . |
| 0 359 697 B1 | 11/1994 | European Pat. Off. . |
| 29 03 357 A1 | 7/1980 | Germany . |
| 40 14 947 A1 | 11/1991 | Germany . |
| 56-108986 | 8/1981 | Japan . |
| 58-58488 | 4/1983 | Japan . |
| WO 96/31790 | 10/1996 | WIPO . |

OTHER PUBLICATIONS

McCormick Laboratories, Inc. brochure entitled "Trachmate Intubation System," 3 pages, dated 1988.

IEEE Transactions on Bio–Medical Engineering, vol. BME–14, No. 4 article, "Magnetic Susceptibility Meter for In Vivo Estimation of Hepatic Iron Stores," pp. 239–243, dated Oct. 1967.

Journal of Medical Engineering & Technology, vol. 11, No. 6 article, "A review of medical applications of magnet attraction and detection," pp. 271–277, dated Nov./Dec. 1987.

IEEE Transactions on Biomedical Engineering, vol. BME–20, No. 6 article, "Design Aids for Simple Magnet Systems Useful in Biomedical Applications," pp. 459–464, dated Nov. 1973.

IEEE Transactions on Biomedical Engineering, vol. MAG–9, No. 3 article, "Magnetic Materials as Biological Implants—Criteria for Selection," pp. 444–447, dated Sep. 1973.

(List continued on next page.)

*Primary Examiner*—Cary O'Connor
*Assistant Examiner*—Eric F. Winakur
*Attorney, Agent, or Firm*—Merchant & Gould P.C.

[57] ABSTRACT

A passive system for accurately determining the location of a device positioned or implanted within a patient's body is disclosed. The system includes a detectable mechanism mounted at the tip of the device which is configured to generate a self-induced magnetic field, and a detector for detecting the magnetic field of the magnet. The detector is detached from the magnet. In a preferred form, the detectable mechanism is a direct current permanent magnet. Methods of using such a system to accurately determine the location of a device within a patient's body are also disclosed.

17 Claims, 12 Drawing Sheets

U.S. PATENT DOCUMENTS

| | | |
|---|---|---|
| 3,757,773 | 9/1973 | Kolin . |
| 4,063,561 | 12/1977 | McKenna . |
| 4,173,228 | 11/1979 | Steenwyk et al. . |
| 4,176,662 | 12/1979 | Frazer . |
| 4,244,362 | 1/1981 | Anderson . |
| 4,249,536 | 2/1981 | Vega . |
| 4,317,078 | 2/1982 | Weed et al. . |
| 4,354,156 | 10/1982 | Kennedy . |
| 4,402,310 | 9/1983 | Kimura . |
| 4,403,515 | 9/1983 | Iwasaki . |
| 4,416,289 | 11/1983 | Bresler . |
| 4,431,005 | 2/1984 | McCormick . |
| 4,432,369 | 2/1984 | Halvorsen . |
| 4,445,501 | 5/1984 | Bresler . |
| 4,526,177 | 7/1985 | Rudy et al. . |
| 4,572,198 | 2/1986 | Codrington . |
| 4,608,992 | 9/1986 | Hakim et al. . |
| 4,619,247 | 10/1986 | Inoue et al. . |
| 4,652,825 | 3/1987 | Redpath et al. . |
| 4,671,287 | 6/1987 | Fiddian-Green . |
| 4,784,646 | 11/1988 | Feingold . |
| 4,790,809 | 12/1988 | Kuntz . |
| 4,804,054 | 2/1989 | Howson et al. . |
| 4,809,713 | 3/1989 | Grayzel . |
| 4,905,698 | 3/1990 | Strohl, Jr. et al. . |
| 4,913,139 | 4/1990 | Ballew . |
| 4,936,281 | 6/1990 | Stasz . |
| 4,943,770 | 7/1990 | Ashley-Rollman et al. . |
| 4,943,775 | 7/1990 | Boskamp et al. . |
| 4,950,987 | 8/1990 | Vranish et al. . |
| 4,976,711 | 12/1990 | Parins et al. . |
| 5,005,592 | 4/1991 | Cartmell ................................. 128/899 |
| 5,056,517 | 10/1991 | Fenici . |
| 5,099,845 | 3/1992 | Besz et al. . |
| 5,134,370 | 7/1992 | Jefferts et al. . |
| 5,171,228 | 12/1992 | McDonald . |
| 5,211,165 | 5/1993 | Dumoulin et al. . |
| 5,253,647 | 10/1993 | Takahashi et al. . |
| 5,257,636 | 11/1993 | White . |
| 5,258,766 | 11/1993 | Murdoch . |
| 5,259,837 | 11/1993 | Van Wormer . |
| 5,271,400 | 12/1993 | Dumoulin et al. . |
| 5,307,808 | 5/1994 | Demoulin et al. . |
| 5,318,025 | 6/1994 | Dumoulin et al. . |
| 5,325,873 | 7/1994 | Hirschi et al. ........................... 128/899 |
| 5,353,795 | 10/1994 | Souza et al. . |
| 5,375,596 | 12/1994 | Twiss et al. . |
| 5,386,828 | 2/1995 | Owens et al. . |
| 5,425,367 | 6/1995 | Shapiro et al. . |
| 5,425,382 | 6/1995 | Golden et al. . |
| 5,426,365 | 6/1995 | Sekihara et al. . |
| 5,622,169 | 4/1997 | Golden et al. ........................... 128/899 |
| 5,762,064 | 6/1998 | Polvani .................................... 600/424 |
| B1 4,905,698 | 10/1991 | Strohl, Jr. et al. . |

OTHER PUBLICATIONS

Magnet Sales & Manufacturing Inc. brochure, High Performance Permanent Magnets, Culver City, California, dated 1993.

Gaston, A. et al., "External Magnetic Guidance of Endovascular Catheters with a Superconducting Magnet: Preliminary Trials", *J. Neuroradiol.*, 15(2):137–147 (1988).

James, A., "Duodenal Intubation with Magnet–Tipped Tubes", *The Lancet*, 209–210 (Jan. 27, 1951).

Ram, W. et al., "Heart Catheterization in a Neonate by Interacting Magnetic Fields: A New and Simple Method of Catheter Guidance", *Catherization and Cardiovascular Diagnosis*, 22:317–319 (Apr. 1991).

Wenger, J. et al., "Magnet–Tipped Tubes for Studies of the Stomach and Duodenum", *Digestive Diseases*, 15(4):383–393 (Apr. 1970).

Williams, J. et al., The Localisation of Enteral Tubes Using a Novel Non–Radiological Technique ("Cathlocator"), *British Society of Gastroenterology*, Abstract No.: T173,. S44 (Date Unknown).

SYSTEMS AND METHODS FOR DETERMINING THE LOCATION OF AN IMPLANTED DEVICE INCLUDING A MAGNET

This is a continuation of application Ser. No. 08/568,629, filed Dec. 7, 1995 now abandoned.

FIELD OF THE INVENTION

The present invention relates generally to systems have methods for determining the location of a device positioned or implanted within the body of a patient. In particular, the present invention relates to systems and methods for determining the intravascular location of a catheter, guide wire, stylet, or other device.

BACKGROUND OF THE INVENTION

Catheters are tubular medical devices which, when inserted into canals, vessels, passageways and the like of a human or animal, permit injection or withdrawal of fluids. In several applications, such as parenteral nutrition, cancer chemotherapy, and frequent antibiotic therapy, the tip of the catheter is typically positioned in areas of high volume blood flow, such as the superior vena cava, to avoid damage to the lining along the blood pathway. During insertion, the catheter may be guided into a wrong passage before it reaches its desired position. In the case of long-term use, it is possible that the catheter may be dislocated from its original position, such as when a patient sneezes. As a result of these occurrences, it is desirable for the caregiver to be able to determine the location of the catheter during initial placement, and at one or more times after placement. This is especially true in the case where the catheter is being placed near vital organs, such as the heart, lungs, and brain.

The caregiver, however, cannot see the catheter once it is implanted within the patient's body. Accordingly, systems and methods for determining the location of the tip of a catheter within a patient's body have been provided. One conventional catheter placement procedure is fluoroscopy, which uses x-ray film. This procedure, however, has many drawbacks. One drawback to this procedure is that the patient and caregivers are exposed to irradiation. In the case of the caregivers, such exposure is often continuous. Another drawback to this procedure is that it is not always accurate. By the time the x-ray is taken, developed and returned, the catheter may have moved. This procedure also requires expensive and bulky equipment that must be operated by trained personnel. In light of the heightened awareness by health care providers to reduce costs, such requirements are undesirable. Yet another disadvantage with this procedure is that it must be performed in the operating room, rather than in a more accessible and convenient doctor's office or examining room.

Another method and device for detecting the tip of a catheter is disclosed in U.S. Pat. No. 4,905,698 to Strohl, Jr. et al. In general, Strohl discloses the use of a source which generates an alternating magnetic field, a detector positioned proximate the distal end of the catheter, and a monitor to which the source and detector are connected. The detector consists of a ferrous core and a pair of leads that are wrapped around the core and fed through the lumen of the catheter to a power source. This method of detection involves phase changes of the induced detector current. By also referencing anatomical landmarks, the caregiver can determine the location of the detector, and thus the tip of the catheter. Once the tip of the catheter is properly positioned, the detector may be removed.

U.S. Pat. No. 4,173,228 to Van Steenwyk et al. also discloses a method and device for detecting the tip of a catheter. Van Steenwyk uses signal intensity to determine the catheter location.

While the Strohl and Van Steenwyk procedures eliminate the need for unnecessary exposure to radiation, they introduce other concerns. The systems disclosed by Strohl and Van Steenwyk are active systems. The detector leads are quite fragile and subject to breakage if not handled with care. The amount of power which can be safely generated within the body is limited. Also, because the detector is in contact with blood or fluids in the body, it must be biologically insulated so that it does not corrode and so that it is not damaged while within the patient's body. The Strohl and Van Steenwyk procedures are not designed for confirming the location of a catheter or other device after placement, thereby limiting its functionality, especially in the case of long-term use.

Thus, a need exists for providing systems and methods of determining the location of an implantable device within the body of a patient which address the concerns of the prior art, such as eliminating the hazards of radiation exposure and the high costs associated with fluoroscopy, eliminating the disadvantages associated with active systems, and/or determining the location of the implantable device on demand.

SUMMARY OF THE INVENTION

The present invention relates to a system for determining the location of a device positioned or implanted within the body of a patient. In one embodiment, the system includes a magnetic field generating mechanism embedded in the tip of the device for generating a self-induced direct current magnetic field, and a detector detached from the generating mechanism for detecting the magnetic field of the generating mechanism so that the location of the device within the patient's body may be accurately determined. The detector may include a directional indicator for providing feedback to the caregiver as to the location of the generating mechanism relative to the detector. Preferably, the generating mechanism is a permanent magnet.

In another embodiment, the detector may include a sensor array mat which can lay either on the patient's body or underneath his or her body, and a tracking monitor connected thereto for processing the location information sensed by the sensor array mat.

Methods for determining the location of a device positioned or implanted within the body of a patient are also disclosed. One method includes the steps of inserting an end of an implantable device into a patient's body, the implantable device having a permanent direct current magnet with a self-induced magnetic field, and directing a detector towards the patient's body for detecting the magnetic field of the magnet so that the location of the tip of the catheter may be determined.

Another method includes the steps of fixing a detector in space relative to the patient's body, inserting an end of an implantable device into the patient's body, the end of the implantable device having a permanent direct current magnet with a self-induced magnetic field, moving the implantable device within the patient's body, and tracking the movement of the implantable device in real time as it is being moved within the patient's body.

These and other features and advantages of the present invention are described in greater detail in the detailed description of the preferred embodiments in connection with the drawings.

DETAILED DESCRIPTION OF THE FIGURES

DETAILED DESCRIPTION OF THE PREFERRED EMBODIMENTS

Figure 1:
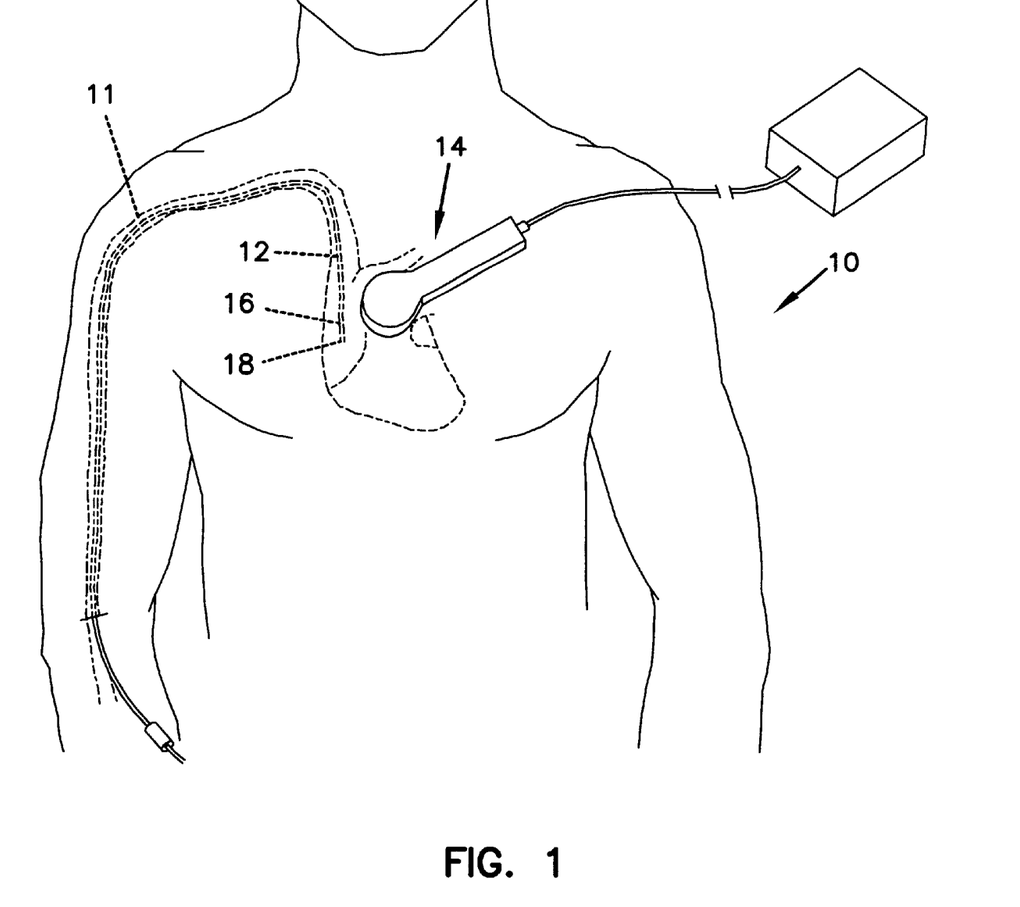
FIG. 1 is a front view of one embodiment of a system for determining the location of a catheter implanted within a patient's body.

A passive system for determining the location of catheters and other devices that are part of an implantable access system within the veins, arteries, or other locations of a patient is shown in FIG. 1 and is generally indicated as system 10. The passive system shown in FIG. 1 includes a catheter implanted in the chest of a patient. While the present invention will be described herein with respect to a chest catheter, it can be appreciated by one skilled in the art that the system can be equally applied to other types of catheters, such as those implanted in the arm, or other devices that are part of an implantable access system within the veins, arteries, or other locations of a patient, such as stylets and guide wires, for example. Other locations within the body where access systems may be positioned include the respiratory tract, the gastro-intestinal tract, or the cerebro-spinal spaces.

Generally, system 10 includes a catheter 12 and a detector 14. Catheter 12 is implanted within the chest of the patient through a tunnel 11 bored within the arm of the patient. As is further shown in FIG. 2, catheter 12 includes a permanent magnet 16 positioned at the tip 18 of catheter 12. Because the magnetic field of magnet 16 is inherent to the material from which it is made, its magnetic field does not need to be induced or generated by an outside source. In addition, because such magnets have a direct current magnetic field (i.e., zero frequency), magnet 16 can effectively block out all signals cause by extraneous electrically powered sources. Finally, because magnet 16 requires no electrical connection, it can be left in the patient so that the location of the catheter can be determined at any time. In one preferred form, magnet 16 is a rare earth magnet or one made from a synthetic compound, such as samarium cobalt (SmCo), neodymium iron boron (NdFeB), or aluminum nickel cobalt (AlNiCo).

Figure 2:
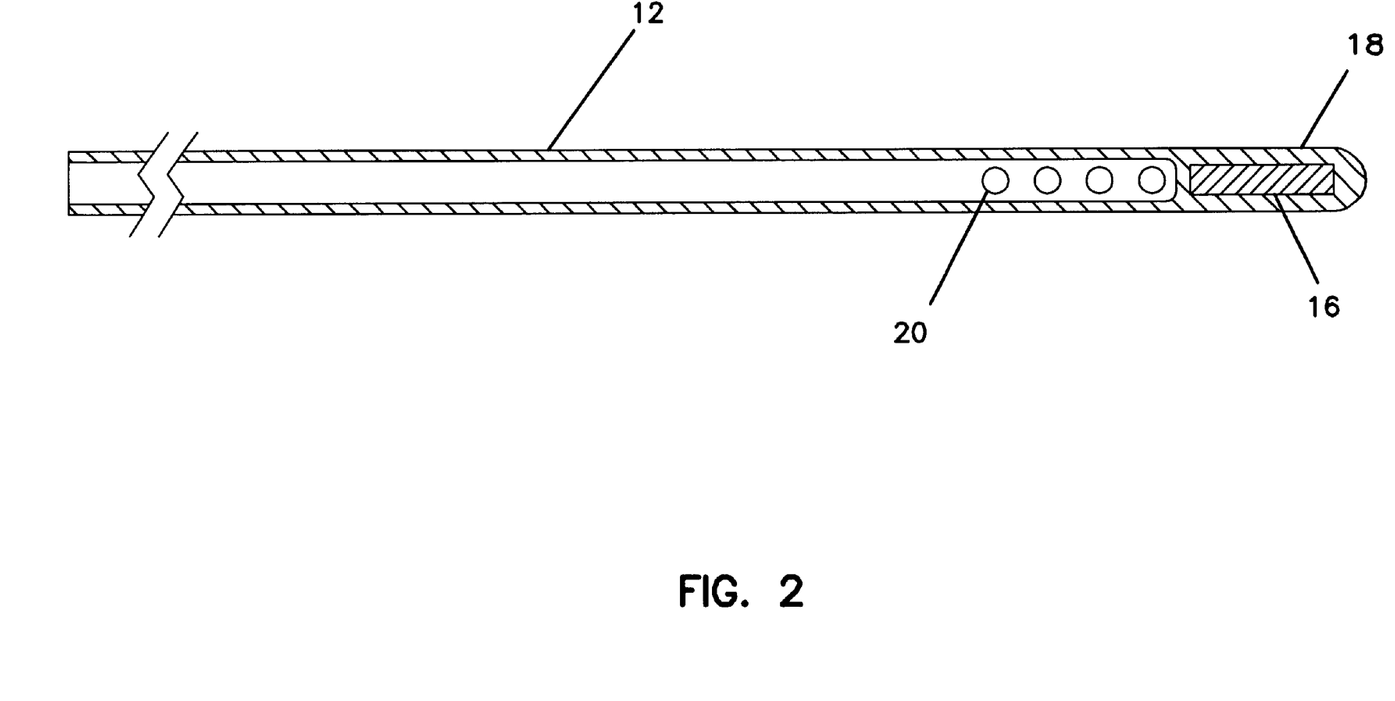
FIG. 2 shows an enlarged cross-sectional view of the distal portion of the catheter of FIG. 1.

The permanent magnet can be positioned within the catheter in several ways. As shown in FIG. 2, magnet 16 may be imbedded in tip 18 of catheter 12 and may be coated with a bio-compatible coating. Since fluids can no longer flow through tip 18 of catheter 12, one or more holes 20 are constructed on the side walls of catheter 12 proximate tip 18 to allow fluids to flow into or out of catheter 12. The size and shape of magnet 16 is preferably small and unobtrusive so that it fits within most catheters.

Figure 3A:
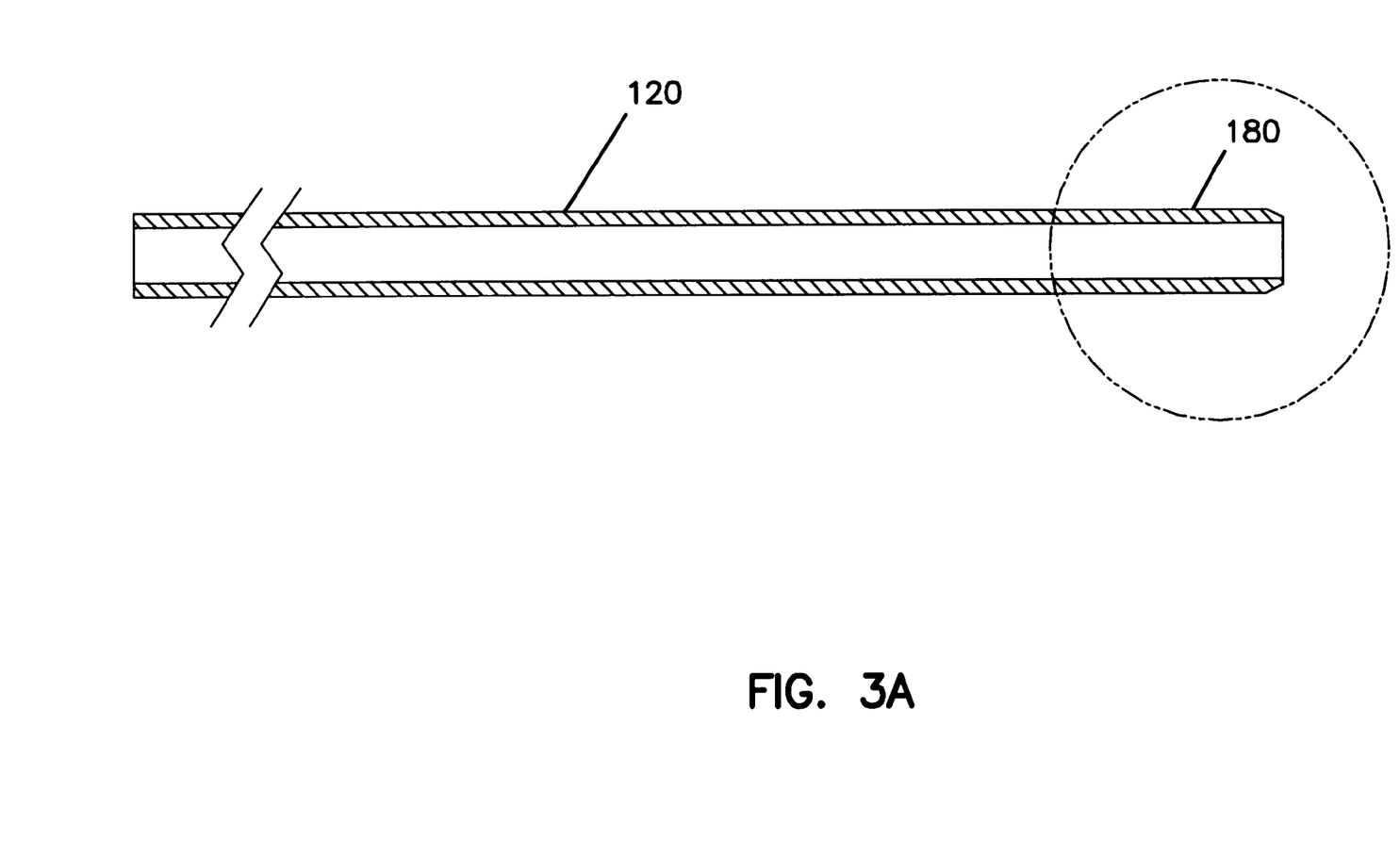
FIGS. 3A and 3B show cross-sectional views of another embodiment of the distal portion of the catheter of FIG. 1.
Figure 3B:
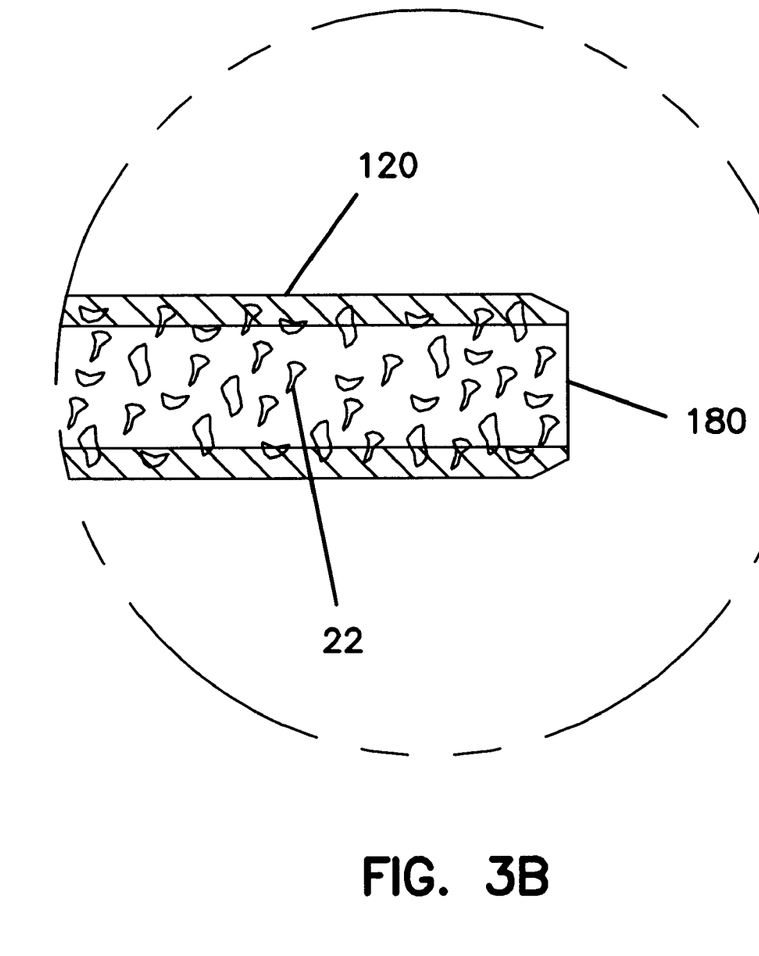

In an alternate embodiment of catheter 120 as is shown in FIGS. 3A and 3B, the permanent magnet consists of a plurality of magnetic particles 22 imbedded in the portion of the side wall of catheter 120 proximate the tip 180. With such a configuration, additional holes do not need to be constructed on the side wall of a catheter 120 since fluids are permitted to freely flow through an end of tip 180. However, each magnetic particle 22 may have to have an increased sensitivity so that the overall sensitivity required to detect the magnetic particles is sufficient.

Figure 4A:
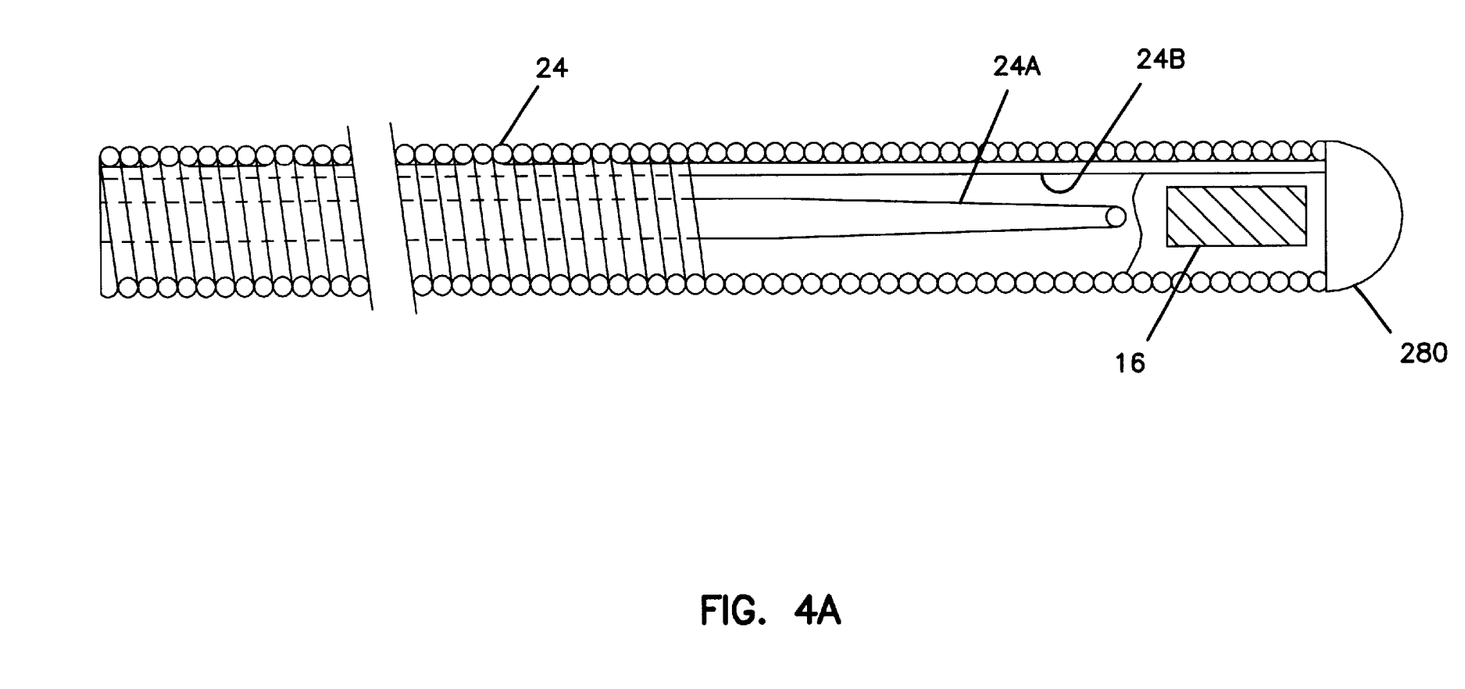
FIGS. 4A, 4B, and 4C show cross-sectional views of a straight, a bent and a J-shaped guide wire, respectively, in accordance with the principles of the present invention.
Figure 4B:
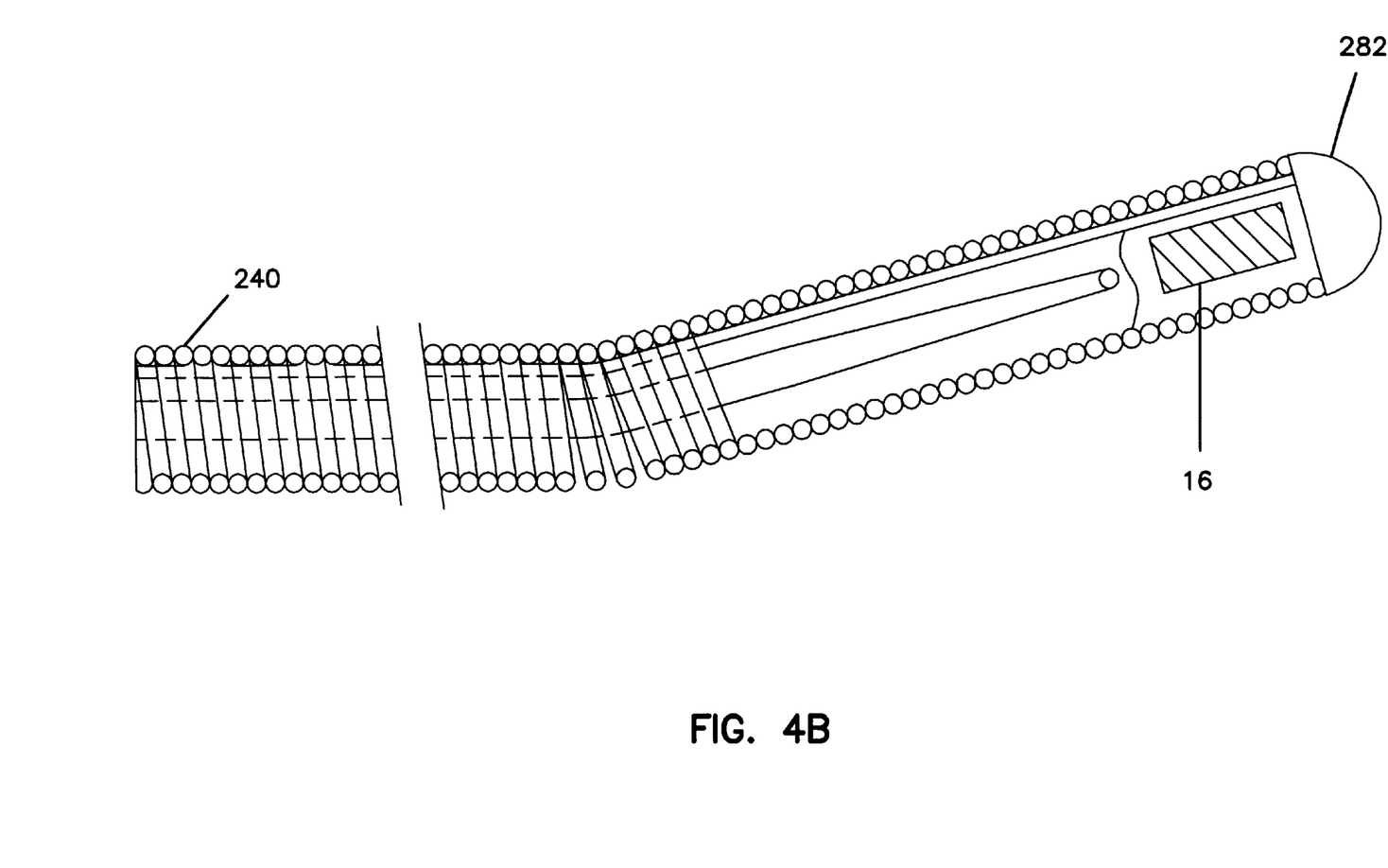
Figure 4C:
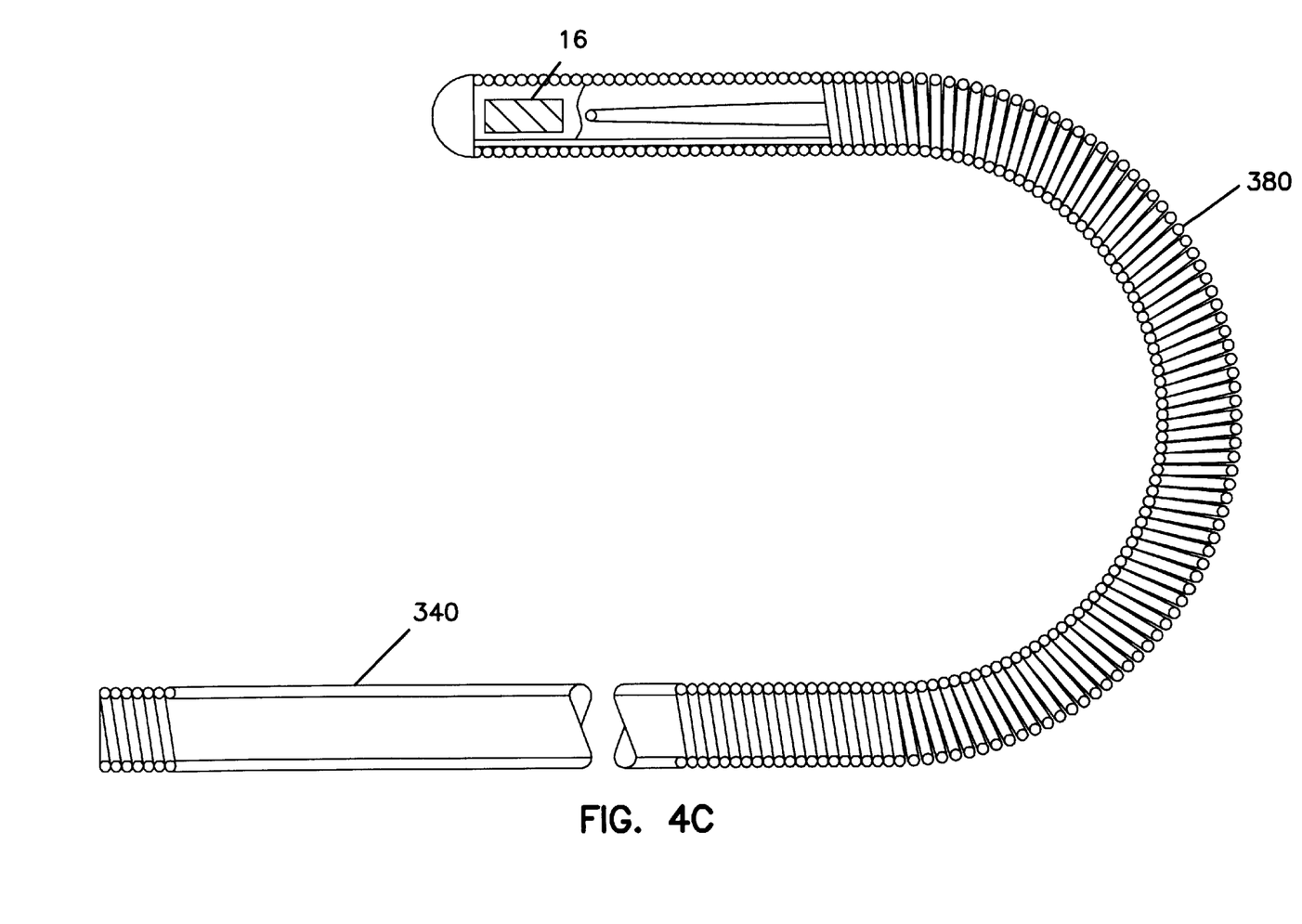

As previously mentioned, the permanent magnet can also be positioned in other devices that are part of an implantable access system. In FIG. 4A, magnet 16 is positioned within the tip 280 of a guide wire 24 having a substantially straight tip 280. Guide wire 24 is a stiffening member that is placed either within the lumen of a catheter or independent thereof, and extends beyond the end of the catheter. Guide wire 24 can occupy the lumen of the catheter or can be placed independent of the catheter. A primary purpose of guide wire 24 is to find the pathway to the desired end destination, typically through the vasculature. Alternately, magnet 16 may be positioned within a guide wire 240 having a bent tip 282 as is shown in FIG. 4B, or a guide wire 340 having a J-shaped tip 380 as is shown in FIG. 4C. Guide wire 24 of FIG. 4A is shown to include an inner tapered core stiffener 24A and a ribbon safety wire 24B to keep guide wire 24 intact during a pulling operation.

Figure 5:
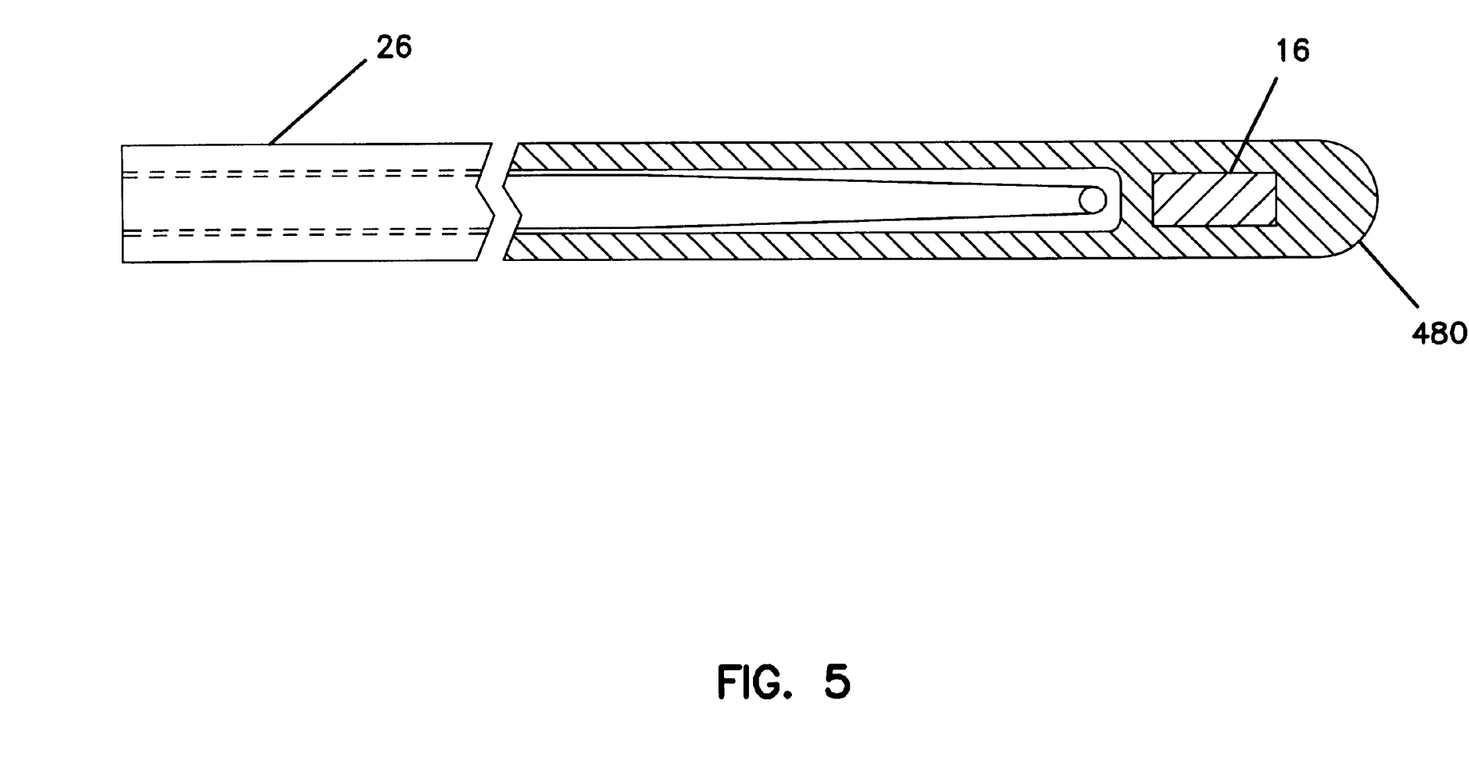
FIG. 5 shows a partial cross-sectional view of a stylet in accordance with the principles of the present invention.

In FIG. 5, magnet 16 is positioned within a stylet 26. Stylet 26 is also a stiffening member with a tip 480, but unlike guide wires 24, 240 and 340, it does not extend beyond the end of the catheter. Stylet 26 gives body to a catheter so that the catheter can be pushed along the vascular system and either cause it to turn or not to bunch up or deflect.

Referring back to FIG. 1, system 10 also includes a detector 14. Detector 14 is preferably of a hand-held size and capable of detecting a magnet at a distance, preferably at least seven (7) inches away. As is shown further in FIG. 6, detector 14 includes a plurality of small magnetic sensors 28 for sensing the magnetic field generated by magnet 16. These sensors produce an electrical voltage in proportion to the strength of the magnetic field. Sensors 28 numbered 1 through N are connected to a meter 29 for measuring the strength (intensity) of the magnetic field detected by sensors 28. Meter 29 displays the magnitude of the voltage and in turn indicates the strength of the magnetic field. By comparing the results of each sensor to another in various combinations, the location of magnet 16 can be determined by vector analysis. The greater number N of sensors 28, the more combinations of readings can be made to determine the location of magnet 16. In one preferred form, sensors 28 numbered 1 through N and meter 29 comprise a Gauss type meter with sufficient sensitivity for sensing magnet 16, and sufficient size so as to not be too cumbersome in a medical environment. As detector 14 is moved towards magnet 16, the strength of the magnetic field measured by meter 29 increases. The location of tip 18 of catheter 12 corresponds to the point at which meter 29 measures maximum magnetic field strength. This mode of operation is known as the wanding mode.

Figure 6:
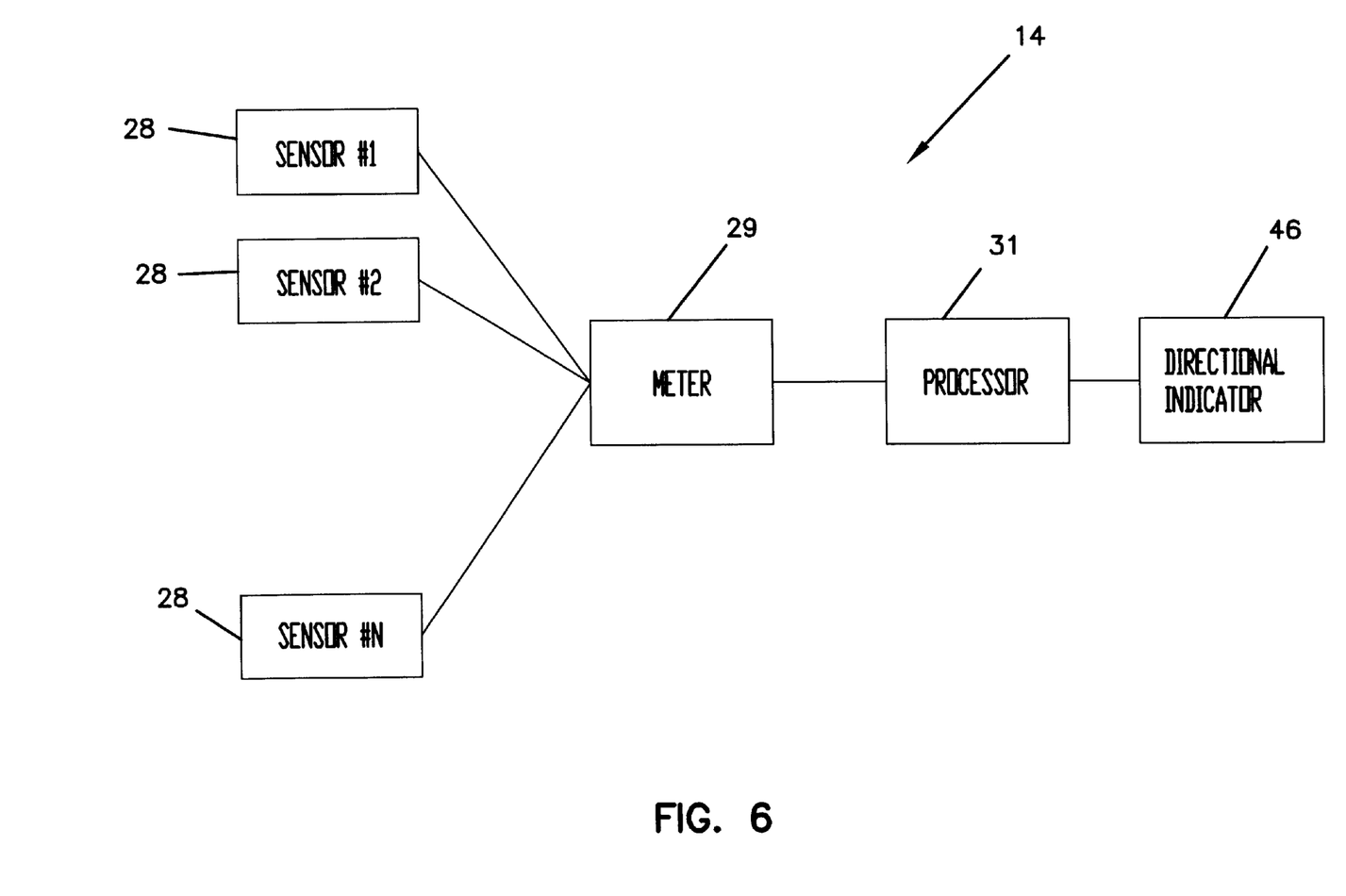
FIG. 6 shows a block diagram representative of the components of the detector of FIG. 1.

Sensors 28 of detector 14 are arranged such that each sensor is of a known spatial relationship to the other sensors.

Sensors 28 are preferably matched (i.e. have like properties) to further insure their accuracy. As detector 14 gets close to tip 18 of catheter 12, each of the sensors 28 detects a field strength from magnet 16. Each sensor will detect the magnetic field of magnet 16 either slightly stronger or weaker than the other sensors. The magnetic field strengths sensed by sensors 28 are measured by meter 29 and input into a processor 31. Since the geometric configurations of sensors 28 are known, processor 31, using vector analysis, determines a vector that points to where magnet 16 is located. As a result, the direction and depth of tip 18 of catheter 12 within the patient can be determined. Various sensors can be used for sensors 28, including current detectors, frequency shift detectors, and flux gates, which are all AC powered. Example sensors 28 useable in system 10 include sensors disclosed in U.S. Pat. Nos. 3,564,402; 3,189,762; and 3,133,244, the disclosures of which are hereby incorporated by reference.

Figure 7A:
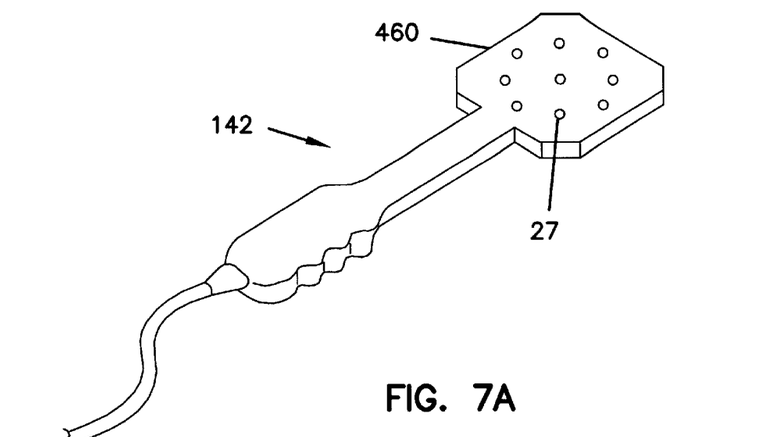
FIGS. 7A, 7B, and 7C show perspective views of several embodiments of the detector of FIG. 6.
Figure 7B:
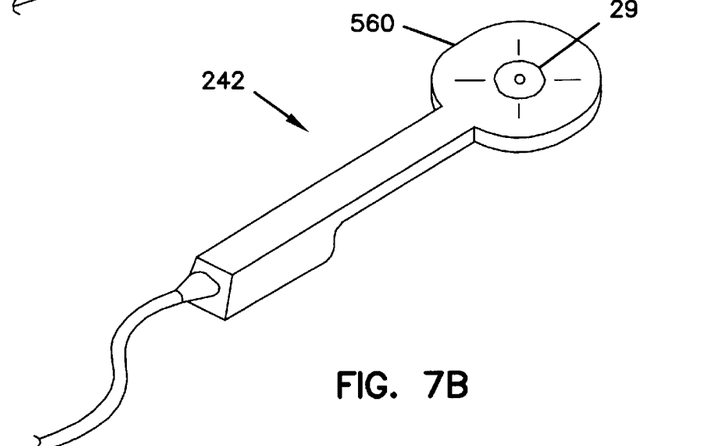
Figure 7C:
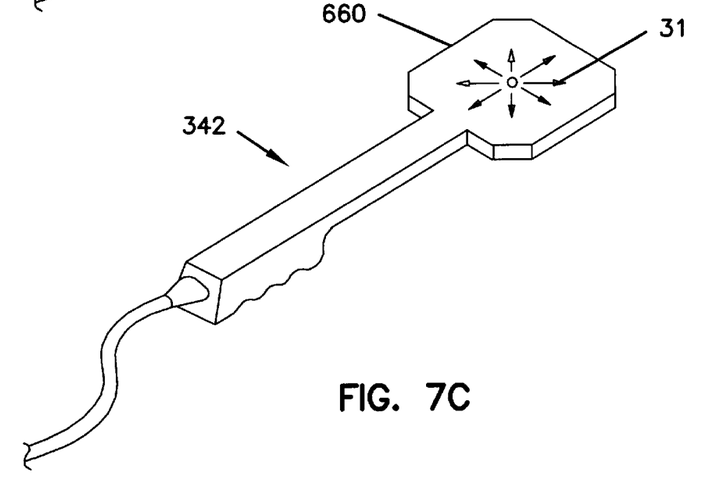

Detector 14 also includes a directional indicator 46 that provides visual and/or audio feedback to the caregiver as to the direction of magnet 16 relative to detector 14. As is further shown in FIGS. 7A–7C, directional indicator 46 can take several forms. In FIG. 7A, detector 142 has a directional indicator 460 in the form of a plurality of radial lights 27. The direction of magnet 16 is indicated by virtue of which light 27 activates. In another embodiment shown in FIG. 7B, detector 242 had a directional indicator 560 in the form of a single light 29. With this embodiment, the direction of magnet 16 can be indicated in several ways, such as by changing the intensity or color of light 29 as detector 14 moves toward and away from magnet 16. In yet another embodiment shown in FIG. 7C, detector 342 has a directional indicator 660 in the form of a plurality of light generating arrows 31. In this embodiment, the direction of magnet 16 is indicated by virtue of which arrow 31 is activated. Preferably, each of the above-described directional indicators provides audio feedback, such as a tone or a beep, when the location of tip 18 of catheter 12 is found.

Figure 8A:
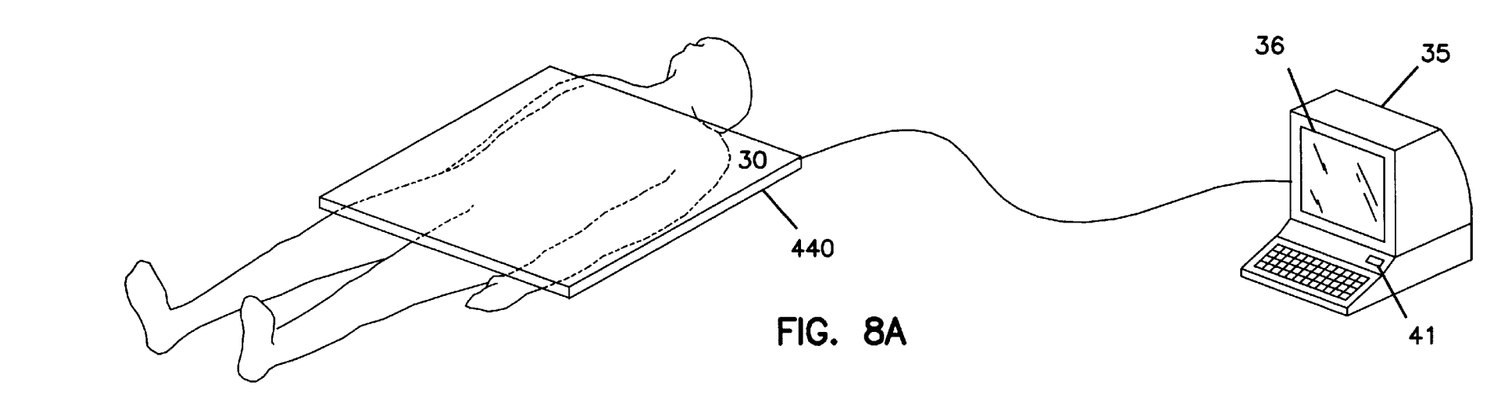
FIGS. 8A and 8B show perspective views of another embodiment of a system for determining the location of a catheter implanted within a patient's body.
Figure 8B:
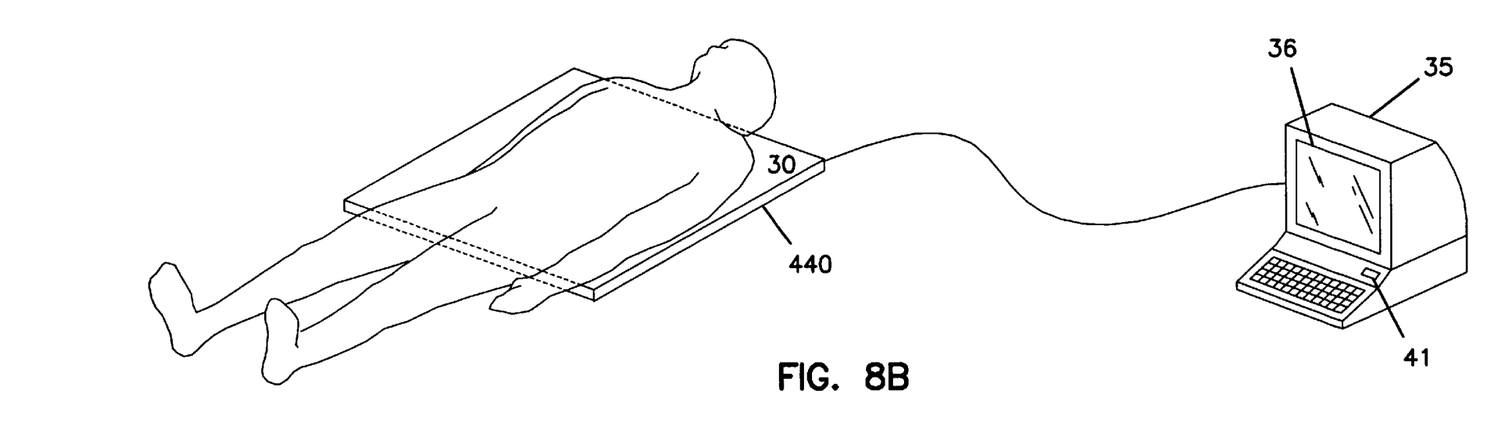

FIGS. 8A and 8B show another mode of operation for determining the location of catheter 12 which involves tracking magnet 16 as it moves within the patient's body. In this mode, a detector 440 is fixed in space and connected to a computer 35 having a tracking monitor 36 which visually tracks magnet 16 as catheter 12 is moved within the body of the patient. Specifically, detector 440 is in the form of a thin, substantially flat mat 30 containing a plurality of magnetic sensors. Mat 30 is positioned adjacent to the patient's body, such as above or below the area where the implanted device is to be positioned. In a preferred form, detector 440 contains a spaced array of at least six sensors. Fifteen combinations of readings from the six sensors can be used in the vector analysis to determine the location of magnet 16. The number of sensors, however, may be increased in order to increase the sensitivity of detector 14 and the area over which catheter 12 may be tracked. A decreased number of sensors is also possible. Computer 35 contains software for processing the information received from mat 30. Mat 30 may be positioned either on top of the patient's chest as is shown in FIG. 8A or beneath the patient's torso as is shown in FIG. 8B. Tracking monitor 36 is preferably a liquid crystal display or CRT.

Figure 9:
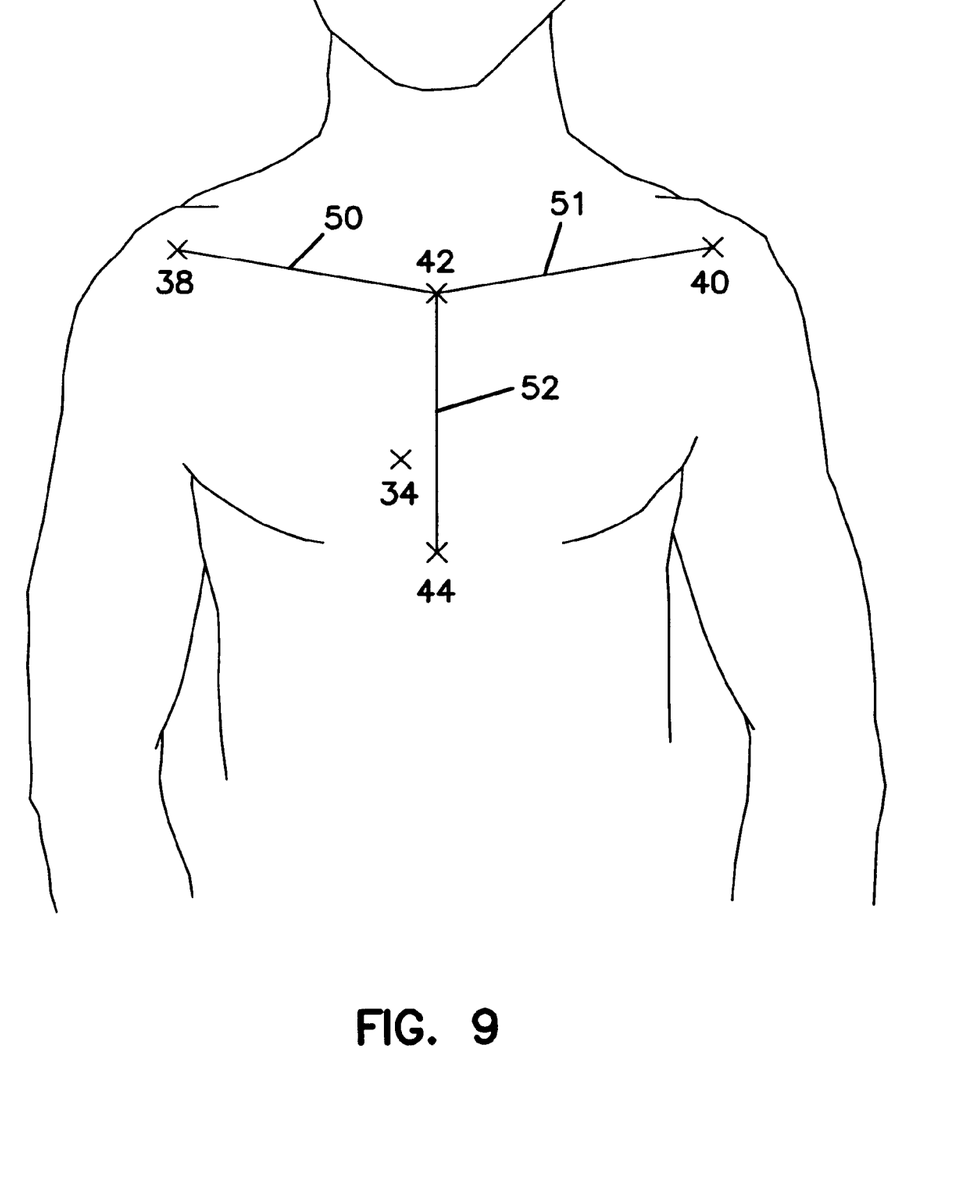
FIG. 9 is a front view of a human torso illustrating magnetic pins in the tracking mode.

One manner in which the tracking mode may be used by a caregiver will now be discussed with reference to FIG. 9. First, the caregiver, based on his or her knowledge of anatomy, goes to the right side of the sternum and counts down three intercostal spaces and places a magnetic pin 34 over this point. The caregiver then presses an activating button 41 on computer 35. Tracking monitor 36 picks up its coordinates (X1, Y1, Z1). A second and third magnet pin 38 and 40 are placed over the right and left shoulder blade, respectively, and upon activation of button 41, tracking monitor 36 picks up another set of coordinates for each pin 38 and 40. A fourth magnetic pin 42 is placed at the small suprasternal notch in the clavicle, and upon activation of button 41, another set of coordinates can be picked up. Finally, a fifth magnetic pin 44 is placed at the very base of the sternum (xyphoid process) where the ribs come into the base of the sternum, and upon activation of button 41, yet another set of coordinates may be determined. Together, the magnetic pins define three lines, namely a line 50 of the right clavicle, a line 51 of the left clavicle, and a line 52 of the sternum. This in turn defines the region of the thorax of interest and divides it into a right and left half.

At each predetermined moment in time, detector 14 calculates a vector based on the strength of the magnetic field detected by detector 14 and indicates the end of the vector as a dot on tracking monitor 36. Monitor 36 preferably updates the information every tenth of a second, so as to provide real time catheter location information. The indication provided on monitor 36 can be of any visual type, such as a flashing light, for example. From the information displayed on tracking monitor 36, the caregiver is able to determine if catheter 12 is going down the correct path.

The tracking mode is especially advantageous because, unlike the wanding mode, there is no relative motion between magnet 16 and detector 440 or other fixed items near the patient. The electronics for subtracting out a moving field is more complex than subtracting out a stationary field. For example, assume that the caregiver is performing a procedure at a hospital where the concrete is reinforced with an iron beam. Under the wanding mode, since there is relative motion between detector 14 and the beam, system 10 may require additional circuitry (e.g., a discriminator circuit) in order to sufficiently discriminate the magnet in the body from the iron beam. This additional circuitry may further complicate the construction of detector 14, and thus increase its costs of manufacture. Without such additional circuitry, the caregiver would have to use his or her common sense and training to eliminate "bad hits" (i.e., items near the patient which clearly cannot be the magnet). When the items are at least six feet away, this determination is relatively easy and accurate. However, when the items are only a few inches away, such a determination may be impossible. As a result, this approach may be less reliable.

Accordingly, the systems and methods described herein reduce or eliminate the deficiencies associated with the prior art. The risks and dangers of exposure to radiation associated with fluoroscopy are eliminated. Because these risks and dangers are eliminated, the present system can be practiced without harm to the patient or caregiver. Because the system is a passive system, no external power source is necessary to generate the magnetic field. Due to the elimination of the need for electrically connecting the magnetic field generating source to a power source, the caregiver's range of motion in performing the necessary procedures is not restricted and exchange procedures are easily facilitated. In exchange procedures, different catheters or other devices may be passed over the same tortuous path in the body. The lack of direct electrical connection with the magnet at the end of the device allows for easier exchange procedures. Because the system can remain within the implantable device, future device location determinations may be performed. The system permits a determination of the location of the tip of the implantable device as a point in space.

Because the system only requires two major components, it is simple to manufacture. The wand directional features and the tracking mode of operation with the use of an array of sensors allow for rapid tip location. These are just a few of the many advantages of the present system and method of detecting the location of a device implanted within a patient's body.

The invention, however, is not to be construed as to be limited by the specific embodiments described above or shown in the drawings, but is to be limited only by the broad general meaning of the following claims.

What is claimed is:

1. A system for determining the location of an implantable device within the body of a patient, comprising:

an implantable device having a tip adapted for insertion into a patient's body;

a generator mechanism positioned at the tip of the implantable device having a self-induced direct current magnetic field;

at least one reference magnet positionable adjacent to the patient's body and having a magnetic field; and a detector detached from the generator mechanism which detects the magnetic field generated by the generator mechanism so that the location of the tip of the implantable device in the patient's body may be determined and which detects the magnetic field of the reference magnet, the detector including a plurality of magnetic sensors arranged in a spaced array and a tracking monitor operatively connected to the sensors, wherein the tracking monitor is configured to visually display a position of the reference magnet and display movement of the tip of the implantable device within the body based on input from the plurality of magnetic sensors, the plurality of magnetic sensors configured for stationary placement relative to the body of the patient.

2. The system of claim 1, wherein the implantable device comprises a catheter.

3. The system of claim 1, wherein the implantable device comprises a stylet.

4. The system of claim 1, wherein the implantable device comprises a guide wire.

5. The system of claim 1, wherein the generator mechanism comprises a permanent magnet.

6. The system of claim 5, wherein the magnet is made of at least one of SmCo, NdFeB, and AlNiCo.

7. The system of claim 5, wherein the magnet is imbedded in the tip of the implantable device, and wherein the implantable device defines a plurality of apertures through which a fluid contained within the implantable device may travel.

8. The system of claim 1, wherein the generator mechanism comprises a plurality of particles of a permanent magnet embedded in the side wall of the implantable device.

9. The system of claim 1, wherein the detector comprises a processor which processes the magnetic fields detected by the detector such that magnetic fields extraneous to the magnetic field generated by the generator mechanism are eliminated.

10. The system of claim 1, wherein the reference magnet includes a plurality of reference magnets positionable adjacent to the patient's body.

11. A method for determining the location of an implantable device within the body of a patient comprising:

fixing a detector in space relative to the patient's body;

establishing at least one reference point by positioning at least one reference magnet adjacent to the patient's body and displaying the reference point visually on a tracking monitor to assist in determining the location of the implantable device within the patient's body;

inserting a tip of an implantable device into a patient's body, the tip of the implantable device having a permanent direct current magnet with a self-induced magnetic field positioned therein;

moving the implantable device in the patient's body; and displaying the movement of the magnet of the implantable device visually on the tracking monitor as it is being moved within the patient's body so that the location of the tip of the device within the patient's body may be determined.

12. The method of claim 11 wherein the detector includes a plurality of magnetic sensors and the step of displaying movement of the magnet further comprises performing vector analysis based on input from the magnetic sensors.

13. The method of claim 11 wherein the step of establishing at least one reference point includes establishing a plurality of reference points by positioning the reference magnet adjacent to the patient's body and displaying the reference points on the tracking monitor to provide points of reference for determining the location of the tip of the implantable device.

14. The method of claim 13 wherein the step of establishing a plurality of reference points comprises positioning the reference magnet in at least two locations to define a line along a clavicle of the patient.

15. The method of claim 13 wherein the step of establishing a plurality of reference points comprises positioning the reference magnet in at least two locations to define a line along a sternum of the patient.

16. A method for determining the location of an implantable device within the body of a patient comprising:

fixing a detector in space relative to the patient's body;

establishing first, second, third and fourth reference points, where the reference points are established by positioning a reference magnet adjacent to the patient's left and right shoulder blades, adjacent to the patient's small suprasternal notch in the clavicle, and adjacent to the base of the patient's sternum, respectively, and displaying each reference point visually on a tracking monitor, to provide points of reference for determining the location of the implantable device within the patient's body;

inserting a tip of an implantable device into a patient's body, the tip of the implantable device having a permanent direct current magnet with a self-induced magnetic field positioned therein;

moving the implantable device in the patient's body;

displaying the movement of the magnet of the implantable device visually on the tracking monitor as it is being moved within the patient's body so that the location of the tip of the device within the patient's body may be determined.

17. A method for determining the location of an implantable device within the body of a patient comprising:

fixing a detector in space relative to the patient's body;

establishing first, second, third, fourth and fifth reference points, where the reference points are established by positioning a reference magnet adjacent to three intercostal spaces down on a right side of the patient's sternum, adjacent to the patient's left and right shoulder blades, adjacent to the patient's small suprasternal notch in the clavicle, and adjacent to the base of the patient's sternum, respectively, and displaying each reference point visually on a tracking monitor, to provide points of reference for determining the location of the implantable device within the patient's body;

inserting a tip of an implantable device into a patient's body, the tip of the implantable device having a permanent direct current magnet with a self-induced magnetic field positioned therein;

moving the implantable device in the patient's body;

displaying the movement of the magnet of the implantable device visually on the tracking monitor as it is being moved within the patient's body so that the location of the tip of the device within the patient's body may be determined, wherein the display of the tracking monitor includes a first segment connecting the second and fourth reference points to define a left clavicle segment, the display further including a second segment connecting the third and the fourth reference points to define a right clavicle segment, and the display further including a third segment connecting the fourth and fifth reference points to define a segment of the sternum.

* * * * *

UNITED STATES PATENT AND TRADEMARK OFFICE
CERTIFICATE OF CORRECTION

PATENT NO. : 5,944,023

DATED : AUGUST 31, 1999

INVENTOR(S) : JOHNSON ET AL.

It is certified that error appears in the above-identified patent and that said Letters Patent is hereby corrected as shown below:

Col. 1, line 10: "have" should read --and--

Signed and Sealed this

Twenty-seventh Day of March, 2001

*Attest:*

*Attesting Officer*

NICHOLAS P. GODICI

*Acting Director of the United States Patent and Trademark Office*